United States Patent [19] [11] 4,162,262
Ellgen et al. [45] Jul. 24, 1979

[54] PROCESS FOR PRODUCING TWO-CARBON ATOM COMPOUNDS FROM SYNTHESIS GAS WITH MINIMAL PRODUCTION OF METHANOL

[75] Inventors: Paul C. Ellgen, Saint Albans; Madan M. Bhasin, Charleston, both of W. Va.

[73] Assignee: Union Carbide Corporation, New York, N.Y.

[21] Appl. No.: 841,054

[22] Filed: Oct. 11, 1977

Related U.S. Application Data

[63] Continuation of Ser. No. 669,480, Mar. 23, 1976, abandoned.

[51] Int. Cl.² .............................................. C07C 27/06
[52] U.S. Cl. ........................ 260/449 R; 260/449.6 R; 260/449.5; 252/454; 252/460; 252/459; 252/458
[58] Field of Search .................... 260/449 R, 449.6 R, 260/449.5

[56] References Cited

U.S. PATENT DOCUMENTS

| | | | |
|---|---|---|---|
| 2,553,398 | 5/1951 | Atwell | 260/449 R |
| 2,583,611 | 1/1952 | Sullivan | 260/449 R |
| 2,616,914 | 11/1952 | Riblett | 260/449 R |
| 3,833,634 | 9/1974 | Pruett et al. | 260/449 R |

FOREIGN PATENT DOCUMENTS 824822  7/1975  Belgium .................................. 260/449

OTHER PUBLICATIONS

Eidus et al., Translated from Izvestiya Akad Nauk SSSR, Seriya Khim, No. 7 (pp. 1160–1169) Jul. 1965, pp. 1129–1135.
Kratel, Doctoral Dissertation, Technical University of Berlin–Charlottenburg 1937, pp. 62–72 done at Kaiser Wilhelm Instit. Mulheim–Ruhr.
Pichler, Brennstoff–Chemie 19, 226–230, 1938.

Primary Examiner—Howard T. Mars
Attorney, Agent, or Firm—Bernard Lieberman

[57] ABSTRACT

A process for selectively preparing a mixture of two-carbon atom oxygenated hydrocarbons while minimizing the co-production of methanol which comprises continuously contacting a gaseous reaction mixture containing hydrogen and carbon monoxide with a solid catalyst comprising rhodium in combination with thorium and/or uranium at reaction conditions correlated so as to favor the formation of a substantial proportion of such two-carbon atom products.

8 Claims, No Drawings

PROCESS FOR PRODUCING TWO-CARBON ATOM COMPOUNDS FROM SYNTHESIS GAS WITH MINIMAL PRODUCTION OF METHANOL

CROSS-REFERENCE TO RELATED APPLICATIONS

This application is a cont. of Ser. No. 669,480, filed Mar. 23, 1976, abandoned.

This application is related to copending U.S. applications Ser. No. 650,799, filed Jan. 20, 1976, U.S. Pat. application Ser. No. 541,660, filed Jan. 16, 1975, U.S. Pat. No. 4,014,913 and describes a method of inhibiting methanol formation with the two-carbon atom compounds produced by the processes described in those applications.

BACKGROUND

This invention concerns an improvement in the selective preparation of two-carbon atom oxygenated hydrocarbons, namely acetic acid, ethanol, and/or acetaldehyde, from synthesis gas. More particularly, the invention concerns reaction of synthesis gas in the presence of a catalyst containing rhodium in combination with thorium and/or uranium to inhibit methanol formation under heterogeneous reaction conditions correlated to produce such two-carbon atom products.

The preparation of hydrocarbons and oxygenated hydrocarbons from synthesis gas (essentially a mixture of carbon monoxide and hydrogen with varying amounts of carbon dioxide) has received extensive study and has achieved commercial adoption. Reaction conditions generally involve temperatures on the order of 150°–450° C., pressures from atmospheric to about 10,000 psig, and hydrogen-to-carbon monoxide ratios in the range of 4:1 to about 1:4, with an iron group or a noble metal group hydrogenation catalyst.

One serious disability of most synthesis gas processes has been the non-selective or non-specific nature of the product distribution. Catalysts which possess acceptable activity generally tend to give a wide spectrum of products, for example, hydrocarbons and oxygenated hydrocarbons having a broad distribution of carbon atom contents. This not only complicates the recovery of desired products, but results in the wastage of reactants to commercially uninteresting byproducts.

Copending application Ser. No. 650,799, and U.S. Pat. No. 4,014,913 are directed to processes for selectively preparing a mixture of two-carbon atom oxygenated compounds, namely, acetic acid, ethanol, and acetaldehyde, using a rhodium catalyst. In Ser. No. 541,660, corresponding to Belgian Pat. No. 824,823 and, there are described processes for shifting the distribution of the aforementioned two-carbon atom products in favor of ethanol relative to acetic acid and acetaldehyde by incorporating elements such as iron, into the rhodium-based catalyst. A characteristic of these modified catalysts is the tendency to show an increased production of methanol which is a less valuable product than the oxygenated two-carbon atom compounds.

SUMMARY OF THE INVENTION

This invention describes a catalyst for the aforementioned process that acts to restrain methanol production while retaining the selectivity of the overall reaction toward two-carbon atom oxygenated compounds. The process of the invention involves contacting synthesis gas with a catalyst comprising rhodium in combination with uranium and/or thorium under suitable reaction conditions.

In a preferred embodiment of the invention, thorium and/or uranium are incorporated into a rhodium catalyst containing one or more of elements, such as iron, molybdenum and tungsten. Such a catalyst exhibits enhanced selectivity to ethanol relative to other two-carbon atom products but with less co-production of methanol.

PROCESS DISCUSSION

The reaction is conducted at reaction conditions of temperature, pressure, gas composition and space velocity correlated so as to collectively produce acetic acid, ethanol, and/or acetaldehyde in an amount which is at least about 50 weight percent, preferably at least about 75 weight percent, of the two and more carbon atom compounds obtained by the reaction. Desirably, the reaction is conducted at these correlated conditions to achieve product efficiencies based on carbon consumption in excess of 10%, and frequently in excess of 50%. By using a suitable catalyst such as rhodium in combination with one or more elements such as iron, molybdenum and tungsten, the reaction may be conducted so that the proportion of ethanol in the two-carbon oxygenated products is at least about 30 percent, and is readily made about 80 percent or more. These catalysts, however, are characterized by increased amounts of methanol and higher molecular weight alcohols in the product as the proportion of ethanol in the two-carbon atom compounds is increased. By incorporating thorium and/or uranium into these rhodium catalysts, the production of methanol can be substantially reduced.

At optimum reaction conditions, and particularly at relatively low conversions, there is little conversion to three-carbon atom and higher hydrocarbons and oxygenated hydrocarbons, and conversion to methane and methanol may be minimized. The reaction efficiency, or selectivity, to the two-carbon atom compounds is invariably at least about 10%, and is usually upwards of about 25%; under the preferred conditions it exceeds 50% and, under optimum conditions, can reach 90% or more. Selectivity is defined herein as the percentage of carbon atoms converted from carbon monoxide to a specified compound or compounds other than $CO_2$.

Thus, the independent reaction variables are correlated so as to favor the formation of a substantial proportion of the desired two-carbon atom oxygenated hydrocarbons (acetic acid, ethanol, and acetaldehyde). This proportion, expressed as carbon conversion efficiency, is usually upwards of 25% and frequently exceeds 50%.

In one aspect of the invention, this correlation is a combination of conditions which result in maintaining moderate reaction conditions to thereby limit the conversion of CO to not more than about one-fourth, preferably not more than about one-eighth. As will be discussed in detail below, this may be achieved primarily by a combination of high space velocity and low temperature, but other factors (e.g., $H_2/CO$ ratio, catalyst activity, pressure, bed geometry, etc.) also affect the conversion. At high conversions, it has been noted that hydrocarbons and higher carbon number oxygenated hydrocarbons are produced in excess, with a resulting loss in efficiency to two-carbon atom compounds.

Conditions of temperature, of pressure, and of gas composition are usually within the ranges that are essentially conventional for synthesis gas conversions, particularly those employed in the production of methanol. Thus, existing technology and, in some instances, existing equipment may be used to effect the reaction.

The reaction is highly exothermic, with both the thermodynamic equilibrium and the kinetic reaction rates being governed by the reaction temperature. Average catalyst bed temperatures are usually within the range of about 150°–450° C., but for optimum conversions, bed temperatures are kept within the range of about 200°–400° C., typically about 250°–350° C.

The reaction temperature is an important process variable, affecting not only total productivity but selectivity toward one or more of the desired two-carbon atom products. Over relatively narrow temperature ranges, as for example 10° or 20° C., an increase in temperature may somewhat increase total synthesis gas conversion, tending to increase the efficiency of ethanol production and decrease the efficiency of acetic acid and acetaldehyde production. At the same time, however, higher temperatures favor methane production, and apparently methane production increases much more rapidly at higher temperatures than do conversions to the more desirable two-carbon atom products. Thus, for a given catalyst and with all other variables held constant, the optimum temperature will depend more on product and process economics than on thermodynamic or kinetic considerations, with higher temperatures tending to increase the production of oxygenated products but disproportionately increasing the co-production of methane.

In the discussions above, the indicated temperatures are expressed as average, or mean, reaction bed temperatures. Because of the highly exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multistage fixed bed adiabatic reactors with inter-stage cooling, or relatively small catalyst particles placed in tube-and-shell type reactors with a coolant fluid surrounding the catalyst-filled tubes. In this regard, reference is made to U.S. application Ser. No. 590,718 filed on June 26, 1975.

The reaction zone pressure is desirably within the range of about 15 psig to about 10,000 psig, economically within the range of about 300–5,000 psig. Higher reaction zone pressures increase the total weight of product obtained per unit time and likewise improve the selectivity toward two-carbon atom compounds.

The ratio of hydrogen to carbon monoxide in the synthesis gas may vary widely. Normally the mole ratio of hydrogen to carbon monoxide is within the range of 20:1 to 1:20, or preferably within the range of about 5:1 to about 1:5. However, in some instances, it may be advantageous to operate with a hydrogen to carbon monoxide mole ratio as low as about 1:200. In most of the experimental work reported herein the mole ratio of the hydrogen to carbon monoxide is about 1:1. Increasing the ratio tends to increase the total rate of reaction, sometimes quite significantly, and has a small though favorable effect on production of two-carbon atom products, but concurrently increases selectivity to methane. Increasing the hydrogen to carbon monoxide ratio also favors the formation of more highly reduced products, that is, ethanol rather than acetaldehyde or acetic acid. Carbon dioxide, normally present in an amount of up to about 10 mole percent in the synthesis gas, has essentially no effect.

One of the features of the present invention is the recognition that a low conversion, e.g., preferably less than 20% of the CO, favors the formation or production of a substantial proportion of acetic acid, ethanol, and/or acetaldehyde, generally in excess of 10%. This conversion is conveniently achieved by employing a high space velocity correlated with other reaction variables (e.g., temperature, pressure, gas composition, catalyst, etc.). Space velocities in excess of about $10^3$ gas hourly space velocity (volumes of reactant gas, at 0° C. and 760 mm mercury pressure, per volume of catalyst per hour, commonly referred to as "GHSV") are generally employed, although it is preferable that the space velocity be within the range of about $10^4$ to about $10^6$ per hour. Excessively high space velocities result in uneconomically low conversions, while excessively low space velocities cause the production of a more diverse spectrum of reaction products, including higher boiling hydrocarbons and oxygenated hydrocarbons.

The rhodium-thorium and rhodium-uranium catalysts are rhodium provided in combination with thorium and/or uranium upon a support material. This is typically effected by depositing rhodium and thorium and/or uranium onto a particulate support material and placing the supported combination into the reaction zone. For purposes of the invention, the catalyst composition may advantageously include other elements, such as, manganese, iron and molybdenum/tungsten, the use of which, in conjunction with rhodium are disclosed, respectively, in copending applications Ser. Nos. 590,717, 541,660.

On the basis of experience to date the amount of catalysts on the support should range from about 0.01 weight percent to about 25 weight percent, based on the combined weight of the metal catalyst and the support material. Preferably, the amount of catalyst is within the range of about 0.1 to about 10 weight percent.

The mole ratio of uranium and/or thorium to rhodium in the catalyst should not be less than 1:1000 (i.e., 0.001) in order to gain some advantage.

A relatively high surface area particulate support, e.g., one having a surface area upwards of about 1.0 square meters per gram (BET low temperature nitrogen adsorption isotherm method), is preferred, desirably upwards of about 10 square meters per gram, although surface area alone is not the sole determinative variable. Based on research to date, silica gel is preferred as the catalyst base or support, with graphite, graphitized carbon, alpha alumina, manganese oxides, magnesia, thorium oxides, uranium oxides, eta-alumina, gamma-alumina, and active carbon being less desirable. Zeolitic molecular sieves, primarily the higher silica-to-alumina crystalline zeolites, also have promise.

For the purpose of this invention, it is believed that rhodium deposited on particles of thorium or uranium oxides, or mixtures thereof, is substantially the same as rhodium in combination with thorium and/or uranium codeposited on any of the above support materials, including the aforementioned oxides of thorium and uranium.

The rhodium and thorium and/or uranium may be deposited onto the base or support by any of the techniques commonly used for catalyst preparation, as for example impregnation from an organic or inorganic solution, precipitation, coprecipitation, or cation exchange (on a zeolite). Conveniently, a solution of a heat decomposable inorganic or organic rhodium compound and a thorium compound and/or a uranium compound is appropriately contacted with the support material, and the support then dried and heated, the latter advantageously under reducing conditions, to form the finely dispersed thorium-or uranium-containing rhodium catalyst. Any of these materials may be deposited concurrently or sequentially. It suffices for the present to say that inorganic or organic rhodium and thorium and/or uranium compounds are appropriately contacted with the support material, and the support then dried and heated, the latter advantageously under reducing conditions, to form the finely dispersed rhodium and manganese.

The rhodium deposited is typically in metal form, desirably as fine discrete particles. The form of the thorium or uranium component is, however, not completely appreciated. It may be chemically associated with the rhodium or it may be in a physical admixture with the rhodium. For example, the thorium or uranium may be alloyed with the rhodium or not, in the form of a metal or an oxidized state of the metal, or it may be in the form of an oxide, a silicate, a carbonate, or the like.

DESCRIPTION OF TEST REACTOR

The reactors used in these studies where either a 316 stainless steel, or an internally gold-plated, bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on March 16-20, 1969 and obtainable from AIChE at 345 East 47th Street, New York, N.Y. 10017. A variable speed, magnetically driven fan continuously recirculated the reaction mixture over the catalyst bed. The following modifications were found to facilitate operation and inhibit run-away methanation reactions.

1. Hydrogen feed gas was introduced continuously at the bottom of the autoclave through the well for the shaft of the Magnedrive agitator.

2. Carbon monoxide feed gas was introduced continuously through a separate port at the bottom of the autoclave, in order to avoid a hydrogen-rich zone in the autoclave.

Effluent gases are removed through a port in the side of the reactor. Condensable liquid products are removed from the exit stream in a brine-cooled condenser at ca. 5° to 10° C. and are collected in a holding tank under pressure. The non-condensable components of the exit stream are vented through a wet test meter at atmospheric pressure to determine their total volume. A rubber septum in the atmospheric pressure line permits syringe sampling of the non-condensable gases. No external recycle is employed.

DESCRIPTION OF THE TEST PROCEDURE

The bulk volume of a weighed catalyst sample is determined, and the sample is placed in the catalyst basket. The quantity of catalyst charged varies from about 4 grams to about 60 grams. The quantity of a particular catalyst to be charged is chosen to give an estimated reactant gas conversion of less than 10 percent. Gold-plated screens and thin layers of glass wool are placed above and below the catalyst bed to prevent circulation of solid fines. The catalyst basket is charged to the reactor, and the reactor is sealed. The sealed reactor and the process lines are pressure tested at ambient temperatures to a pressure about 500 to 1000 psig in excess of the maximum anticipated working pressure. Nitrogen, hydrogen, or a mixture of the two is used for this test.

When the reactor is shown to be leak free, pure hydrogen is passed through the reactor, and the temperature is raised to about 240° C. The hydrogen and carbon monoxide flows are then adjusted to give the desired steady-state ratio at the desired approximate purge rate. The purge rate is typically from about 250 STP* liters/hr to about 800 STP* liters/hr. The hydrogen-carbon monoxide ratio is determined by gas chromatographic analysis of an effluent gas aliquot.

* "STP" means standard temperature and pressure defined as 0° C. and 1 atm. pressure.

When the appropriate gas composition is obtained, the reactor temperature is raised to the value desired. A period from about 0.5 hour to about one hour is allowed for the reactor to reach a steady-state at the new temperature. The liquid product trap is then drained, a wet test meter reading is taken, and the time is noted as the beginning of a run. During the course of a run, one or more effluent gas samples are analyzed for hydrogen, carbon monoxide, acetaldehyde, methane, and other volatile hydrocarbons. At the end of a run, the liquid product is collected, and the volume of effluent gas is noted. The liquid product is analyzed by gas chromatography.

Succeeding runs with the same catalyst may be made either at the same conditions or at new conditions of temperature or feed gas flow rates. If any of these conditions are changed, approximately one hour is allowed for the reactor to come to a new steady-state before beginning a new run.

PREPARATION OF CATALYSTS

Catalysts cited in Table I below were all prepared by essentially the following sequence of steps: The desired quantities of rhodium trichloride or rhodium (III) nitrate, and one or more of thorium (IV) nitrate, uranyl nitrate, ammonium heptamolybdate tetrahydrate, ammonium metatungstate and manganese (II) nitrate, depending upon the desired catalyst composition, were dissolved in distilled water at ambient temperature. The volume of distilled water taken for the preparation of this solution was chosen to just fill the void volume (pores) of the support sample being impregnated. Davison TM Grade 59 silica gel (8-20 mesh-U.S. Sieves) was placed in a vacuum flask. The top of the flask was sealed with a rubber septum, and the flask was evacuated through the side arm. A syringe needle was then used to inject the solution onto the evacuated support. When addition was complete, the impregnated support was allowed to stand at one atmosphere for ca. 30 minutes. It was then carefully dried in a nitrogen atmosphere using the following sequence: 80° C. (for 1 hr.); 110° C. (2 hrs.); 150° C. (2 hrs.); 250° C. (2 hrs.). The dried, impregnated support was placed in a quartz tube through which hydrogen was continuously passed. The temperature was raised from 100° to 500° C., over a six hour period and then held at 500° C. for 1 hour. The reduced catalyst was cooled to ambient temperature in an atmosphere of flowing nitrogen or hydrogen.

Tables I and II below summarize the data for a series of silica-gel supported rhodium catalysts containing one or more of the following elements: thorium, uranium, manganese, iron, zinc, tungsten and molybdenum. The catalysts were tested at 300° C., 1000 psig total pressure, and a hydrogen to carbon monoxide mole ratio of about unity, according to the aforementioned test procedure in the above-described test reactor. Ethyl esters and acetates which were formed were included as ethanol and acetic acid in determining productivities and selectivities as used in the data presented herein shown in the tables below. That is, in calculating ethanol and acetic acid values, credit was taken for quantities obtainable by hydrolyses of esters determined to be present.

Examples A and B in Table I teach that rhodium-iron catalysts have high ethanol preference ratios, and that catalysts which exhibit such high preference ratios tend also to exhibit high carbon efficiencies to methanol.

Examples C–F constitute a set of experiments designed to screen the effect of adding thorium, uranium, and zinc to a rhodium-iron catalyst. These examples teach that the presence of thorium and/or uranium in the catalyst tends to reduce the carbon efficiency to methanol and that the presence of zinc adversely affects catalyst activity.

Examples G and H demonstrate that the addition of thorium or uranium to a rhodium-iron catalyst combines the advantages of a high synthesis rate for two-carbon oxygenated chemicals, a high ethanol preference ratio, and a reduced carbon efficiency to methanol relative to rhodium-iron catalysts.

Examples I-P teach that catalysts containing rhodium, iron, thorium, uranium and manganese exhibit relatively high syntheses rates to two-carbon oxygenated chemicals, high ethanol preference ratios, and reduced carbon efficiencies to methanol relative to rhodium-iron catalysts.

The activity of rhodium-thorium and rhodium-uranium catalysts are shown in examples Q-T. These examples demonstrate that thorium and/or uranium are used to best advantage in combination with other additives which enhance the kinetics of the rhodium-catalyst with regard to two-carbon atom chemicals and are particularly selective for ethanol formation.

Examples 1–8 of Table II illustrate, in a general way, the effect of uranium and thorium on an otherwise ethanol-selective catalyst characterized by the co-production of substantial amounts of methanol. Specifically, uranium and thorium were added separately and in combination to rhodium-based catalysts containing molybdenum and tungsten. The carbon efficiency to methanol was markedly lower for those catalysts which contained thorium or uranium relative to those which did not.

TABLE I
USE[a] OF THORIUM AND URANIUM TO SUPPRESS METHANOL FORMATION IN ETHANOL-SELECTIVE CATALYSTS

| Example | Catalyst % Rh | % Fe | % Th | % U | % Zn | % Mn | Dispersion[b] % | Carbon Efficiency, %[c] Hydrocarbon[g] | Methanol | Ethanol[d] | n-Propanol | n-Butanol | Acetaldehyde | Acetic Acid[d] | Ethanol Preference Ratio[e] | Rate to $C_2$ Products (lb/cf/hr)[f] |
|---|---|---|---|---|---|---|---|---|---|---|---|---|---|---|---|---|
| A | 2.5 | .68 | 0. | 0. | 0. | 0. | 13.8 | 40. | 29. | 28. | 2.1 | .1 | .68 | .84 | 18. | 3.5 |
| B | 2.5 | 1.33 | 0. | 0. | 0. | 0. | 5.4 | 53. | 19. | 23. | 2.2 | .4 | .56 | .62 | 20. | 2.5 |
| C | 2.5 | .68 | .044 | .044 | .05 | 0. | 12.9 | 49. | 18. | 29. | 2.1 | .4 | .72 | .78 | 19. | 2.7 |
| D | 2.5 | .68 | .044 | .44 | .5 | 0. | 10.1 | 75. | 10. | 12. | 1.6 | .2 | .30 | .09 | 31. | .21 |
| E | 2.5 | .68 | .44 | .44 | .05 | 0. | 20.7 | 51. | 7.6 | 36. | 2.0 | .8 | 1.2 | 1.4 | 14. | 3.9 |
| F | 2.5 | .68 | .44 | .044 | .5 | 0. | 14.1 | 57. | 21. | 19. | 2.0 | .5 | .49 | .09 | 33. | .19 |
| G | 2.5 | .68 | 1.33 | 0 | 0. | 0. | 8.4 | 48. | 8.9 | 36. | 2.0 | .8 | 1.3 | 2.0 | 11. | 4.5 |
| H | 2.5 | .68 | 0. | 1.33 | 0. | 0. | 4.2 | 55. | 4.2 | 30. | 2.2 | 1.0 | 3.8 | 2.4 | 4.8 | 3.7 |
| I | 2.5 | .68 | .88 | .22 | 0. | .8 | 14.7 | 51. | 3.3 | 36. | 1.6 | .6 | 2.1 | 4.4 | 5.5 | 6.3 |
| J | 2.5 | .68 | .22 | .89 | 0. | .8 | 17.2 | 56. | 1.6 | 30. | 2.0 | 1.9 | 2.7 | 4.2 | 4.3 | 6.2 |
| K | 2.5 | .68 | .88 | .89 | 0. | .2 | 18.0 | 49. | 4.5 | 36. | 2.1 | 1.1 | 2.5 | 3.8 | 5.7 | 4.5 |
| L | 2.5 | .68 | .22 | .22 | 0. | .2 | 16.8 | 43. | 6.9 | 39. | 2.6 | 2.1 | 2.1 | 3.3 | 7.2 | 3.9 |
| M | 2.5 | .2 | .44 | .44 | 0. | .1 | 6.7 | 48. | 3.1 | 36. | 1.5 | 0. | 5.0 | 5.8 | 3.3 | 3.4 |
| N | 2.5 | .4 | .44 | 1.8 | 0. | .1 | 15.6 | 51. | 2.1 | 34. | 2.3 | .1 | 6.0 | 4.2 | 3.3 | 6.1 |
| O | 2.5 | .2 | 1.8 | 1.8 | 0. | 1. | 21.2 | 45. | 1.2 | 32. | 1.9 | .8 | 7.7 | 9.9 | 1.8 | 7.3 |
| P | 2.5 | .4 | .44 | .089 | 0. | 1. | 10.4 | 47. | .92 | 36. | 2.8 | 2.9 | 5.4 | 4.8 | 3.5 | 5.5 |
| Q | 2.5 | 0. | 1.0 | 0. | 0. | 0. | 31.0 | 31. | 1.7 | 28. | .8 | 0. | 18. | 19. | .76 | 3.6 |
| R | 2.5 | 0. | 2.5 | 0. | 0. | 0. | 29.9 | 35. | 1.4 | 23. | .7 | 0. | 23. | 15. | .61 | 5.2 |
| S | 2.5 | 0. | 0. | 1.0 | 0. | 0. | 24.2 | 43. | 2.3 | 26. | 1.1 | 0. | 13. | 11. | 1.1 | 2.1 |
| T | 2.5 | 0. | 0. | 2.5 | 0. | 0. | 16.9 | 36. | 1.1 | 23. | .8 | 0. | 22. | 16. | .61 | 5.0 |

FOOTNOTES FOR TABLE I
[a]Data are from experiments at 300° C. and 1000 psig. The off gas contains approximately 50% CO, 50% $H_2$. Limits shown are average deviations for multiple (usually two) tests. Catalysts contain the indicated nominal weight percentages of rhodium and other elements supported on Davison™ Grade 59 Silica Gel.
[b]Dispersion is defined as the fraction of the metal atoms present in the catalyst which are present at the surface of metal crystallites and so are accessible to gas phase molecules. It is measured by determining the number of moles of CO which will chemisorb on a given quantity of catalyst. These analytical procedures are described by S. J. Gregg and K. S. Sing, Adsorption, Surface Area, and Porosity (Academic Press, Inc., New York, 1967), where CO adsorption is described at pages 263-267 and the dynamic gas chromatographic technique is described at pages 339-343. In this table, the dispersion given is calculated on the assumptions that rhodium chemisorbs one molecule of CO per atom of metal exposed but that other elements do not chemisorb CO at all.
[c]Percent carbon efficiency to a particular product is defined as 100 times the number of moles of carbon present in that product divided by the number of moles of CO converted to products other than $CO_2$.
[d]Values given in this table for ethanol and for acetic acid include quantities actually present as ethyl esters and as acetates, respectively.
[e]The ethanol preference ratio is the carbon efficiency to ethanol divided by the sum of the carbon efficiency to acetaldehyde and the carbon efficiency to acetic acid.
[f]Units are total pounds of ethanol plus acetic acid plus acetaldehyde produced per cubic foot of catalyst per hour.
[g]Hydrocarbon is aggregated methane, ethane, ethylene, propane, propylene, butane, butenes, and water - soluble oil.

TABLE II
RHODIUM-BASED CATALYSTS FOR THE SYNTHESIS OF ETHANOL[a]

| Example | Catalyst % Rh | % Mo | % W | % U | % Th | Dispersion[b] % | Carbon Efficiency, % (C) Gas CH₄ | Gas HC[d] | Meth-anol | Ethan-ol[e] | n-Prop-anol | n-But-anol | n-Pent-anol | Acetal-dehyde | Acetic Acid[e] | Ethanol Preference Ratio[f] | Rate to C₂ Products (lb/cf/hr)[g] |
|---|---|---|---|---|---|---|---|---|---|---|---|---|---|---|---|---|---|
| 1 | 2.5 | .2 | .2 | 0. | 0. | 26.3 | 36. | 14. | 5.1 | 28. | 6.6 | 4.1 | .11 | 2.4 | 3.4 | 4.9 | 11.6 |
| 2 | 2.5 | .8 | .2 | 0. | .2 | 18.9 | 33. | 6. | 2.5 | 31. | 1.5 | 0.0 | .07 | 9.4 | 15.4 | 1.3 | 6.0 |
| 3 | 2.5 | .2 | .8 | 0. | .2 | 21.8 | 39. | 15. | 1.8 | 22. | 3.2 | .4 | .50 | 6.0 | 10.3 | 1.3 | 10.7 |
| 4 | 2.5 | .8 | .8 | 0. | .2 | 9.2 | 40. | 13. | 20. | 19. | 4.2 | 1.1 | .25 | 0.2 | 1.4 | 11.4 | 7.7 |
| 5 | 2.5 | .2 | .2 | .2 | .2 | 27.0 | 42. | 8. | 1.2 | 24. | 1.5 | 0.0 | .08 | 7.8 | 14.7 | 1.1 | 15.0 |
| 6 | 2.5 | .8 | .2 | .2 | 0. | 15.8 | 44. | 16. | 4.8 | 23. | 4.9 | 0.0 | .45 | 1.7 | 5.1 | 3.4 | 12.0 |
| 7 | 2.5 | .2 | .8 | .2 | 0. | 18.9 | 46. | 22. | 2.7 | 16. | 4.3 | 0.0 | .29 | 1.3 | 6.2 | 2.1 | 11.1 |
| 8 | 2.5 | .8 | .8 | .2 | .2 | 17.6 | 48. | 9. | 0.9 | 19. | 1.2 | 0.0 | 0. | 9.0 | 12.0 | .9 | 13.0 |

FOOTNOTES FOR TABLE II
[a]Data are from experiments at 300° C. and 1000 psig. The off gas contains approximately 50% C, 50% H₂. Limits shown are average deviations for multiple (three to five) tests. Catalysts contain the indicated nominal weight percentages of rhodium and other elements supported on Davison™ Grade 59 Silica Gel.
[b]Dispersion is defined as the fraction of the metal atoms present in the catalyst which are present at the surface of metal crystallites and so are accessible to gas phase molecules. It is measured by determining the number of moles of CO which will chemisorb on a given quantity of catalyst. These analytical procedures are described by S. J. Gregg and K. S. Sing, Adsorption, Surface Area, and Porosity (Academic Press, Inc., New York, 1967), where CO adsorption is described at pages 263–267 and the dynamic gas chromatographic technique is described at pages 339–343. In this table, the dispersion given is calculated on the assumtions that rhodium chemisorbs one molecule of CO per atome of metal exposed but thatother elemets do not chmeisort CO at all.
[c]Percent carbon efficiency to a particular product is defined as 100 times the number of moles of carbon present in that product divided by the number of moles of CO converted to products other than CO₂.
[d]"Gas HC" comprises two-, three-, and four-cargon paraffins and olefins present in the uncondensed portion of the reactor effluent ("bolw-off gas").
[e]Values given in this table for ethanol and for acetic acid include quantities actually present as ethyl esters and as acetates, respectively.
[f]The ethanol preference ratio is the carbon efficiency to ethanol divided by the sum of the carbon efficiency to acetaldehyde and the carbon efficiency to acetic acid.
[g]Units are total pounds of ethanol plus acetic acid plus acetaldehyde porduced per cubic foot of catalyst per hour.

What is claimed is:

1. In a process for the reaction of a synthesis gas containing carbon monoxide and hydrogen in the presence of a hydrogenation catalyst, the improvement for selectively producing two-carbon atom oxygenated hydrocarbon products while minimizing the production of methanol which comprises continuously contacting said synthesis gas with a heterogeneous catalyst comprising rhodium in combination with at least one element selected from the group consisting of thorium and uranium, the mole ratio of uranium and/or thorium to rhodium being at least 1:1000, at reaction conditions such that product efficiencies based on carbon consumption in excess of 10 percent are achieved and ethanol, acetic acid and acetaldehyde are formed in an amount which is at least about 50 weight percent of the two or more carbon atom compounds obtained by the reaction, and the conversion of CO is limited to no more than about one-fourth, whereby the production of methanol is reduced such that the carbon efficiency to methanol is lower than the corresponding carbon efficiency when thorium and uranium are absent from the catalyst, which reaction conditions include a temperature within the range of from about 150°–450° C., a pressure within the range of from about 15–10,000 psig, and a mole ratio of hydrogen to carbon monoxide within the range of from about 20:1 to 1:200.

2. Process of claim 1 wherein said reaction conditions include a temperature within the range of about 250°–350° C., a pressure within the range of about 300–5,000 psig, and a mole ratio of hydrogen to carbon monoxide within the range of about 5:1 to 1:5.

3. Process of claim 1 wherein the space velocity of the synthesis gas is in excess of about $10^3$ GHSV.

4. Process of claim 3 wherein said space velocity is within the range of about $10^4$ to $10^6$ GHSV.

5. The process of claim 1 wherein said catalyst additionally contains manganese.

6. The process of claim 1 wherein said catalyst additionally contains molybdenum or tungsten.

7. The process of claim 1 wherein said catalyst additionally contains iron.

8. The process of claim 6 wherein said reactive conditions include a temperature within the range of about 250°–350° C., a pressure within the range of about 300–5,000 psig, and a mole ratio of hydrogen to carbon monoxide within the range of about 5:1 to 1:5.

* * * * *

UNITED STATES PATENT AND TRADEMARK OFFICE
CERTIFICATE OF CORRECTION

PATENT NO. : 4,162,262
DATED : July 24, 1979
INVENTOR(S) : Paul C. Ellgen and Madan M. Bhasin It is certified that error appears in the above-identified patent and that said Letters Patent are hereby corrected as shown below:

Column 9, Footnote (b), first line, for Table I,

"accesible" should read -- accessible --.

Column 11, Footnote (b), third line, for Table II,

"assumtions" should read -- assumptions --.

Column 11, Footnote (b), fourth line, for Table II,

"thatother elemets" should read

-- that other elements --.

Column 11, Footnote (b), fourth line, for Table II,

"chmeisorb" should read -- chemisorb --.

UNITED STATES PATENT AND TRADEMARK OFFICE
CERTIFICATE OF CORRECTION

PATENT NO. : 4,162,262
DATED : July 24, 1979
INVENTOR(S) : Paul C. Ellgen and Madan M. Bhasin It is certified that error appears in the above-identified patent and that said Letters Patent are hereby corrected as shown below:

Column 11, Footnote (d) for Table II,

"cargon" should read -- carbon --.

Column 11, Footnote (d) for Table II,

"("bolw-off gas")." should read

--("blow-off gas"). --.

Signed and Sealed this

Twenty-third Day of October 1979

[SEAL]

Attest:

RUTH C. MASON
Attesting Officer

LUTRELLE F. PARKER
Acting Commissioner of Patents and Trademarks